United States Patent [19]

Blaszczak

[11] 4,320,055
[45] Mar. 16, 1982

[54] PROCESS FOR PENICILLIN EPIMERIZATION

[75] Inventor: Larry C. Blaszczak, Indianapolis, Ind.

[73] Assignee: Eli Lilly and Company, Indianapolis, Ind.

[21] Appl. No.: 138,022

[22] Filed: Apr. 7, 1980

[51] Int. Cl.$^3$ ............................................. C07D 499/04
[52] U.S. Cl. .................................. 260/239.1; 544/30; 544/90
[58] Field of Search ....................................... 260/239.1

[56] References Cited

U.S. PATENT DOCUMENTS 3,719,667  3/1973  Gutowski ........................ 260/239.1
3,954,734  5/1976  Doub et al. ..................... 260/239.1

OTHER PUBLICATIONS

Pant et al., *J. C. S. Chem. Comm.*, pp. 57–58, (1977).
Vlietinck et al. I, *Tet. Letters*, No. 4, pp. 285–287, (1972).
Kovacs et al., *Acta. Chem. Scand.*, 27, pp. 677–704, (1973).
Class et al., *J. C. S. Perkin I*, pp. 932–937, (1973).
Vlietinck et al. II, *J. C. S. Perkin I*, pp. 937–942, (1973).
Barton et al., *J. C. S. Perkin I*, pp. 599–603, (1973).
Vlietinck et al. III, *J. Org. Chem.*, vol. 39, No. 4, pp. 441–444, (1974).
Fukumura et al., *Tet. Letters*, pp. 4123–4126, (1975).
Busson et al., *J. Org. Chem.*, vol. 41, No. 15, pp. 2561–2565, (1976).
Wolfe et al., *Chem. Comm.*, 242–244, (1968).
Johnson et al., *Tet. Letters*, No. 16, pp. 1903–1905, (1968).
Sassiver et al., *Tet. Letters*, No. 45, 3993–3996, (1969).
Cooper et al., *J. Amer. Chem. Soc.*, 91, pp. 1528–1529, (1969).
Gutowski, *Tet. Letters*, No. 21, pp. 1779–1782, (1970).
Stoodley et al. I, *J. C. S. Perkin I*, pp. 450–452, 647–648, (1971).
Jackson et al., *J. C. S. Perkin I*, pp. 895–899, (1972).

*Primary Examiner*—Natalie Trousof
*Assistant Examiner*—Vera C. Clarke
*Attorney, Agent, or Firm*—William B. Scanlon; Arthur R. Whale

[57] ABSTRACT

6$\beta$-acylaminopenicillin-1$\beta$-sulfoxides are epimerized to 6$\alpha$-acylaminopenicillin-1$\beta$-sulfoxides using triethylamine and chlorotrimethylsilane. The 6$\alpha$-acylaminopenicillin-1$\beta$-sulfoxides produced in this process are useful intermediates in the synthesis of 7$\beta$-acylamino-7$\alpha$-alkoxy-3-methyl 1-oxa $\beta$-lactam acids, a class of 1-oxa $\beta$-lactam antibiotics.

52 Claims, No Drawings

PROCESS FOR PENICILLIN EPIMERIZATION

BACKGROUND OF THE INVENTION

The invention claimed in this application is an improvement over previous processes for the C-6 epimerization of penicillin sulfoxides. Specifically, the process of this invention is a highly efficient process (i.e., 80% yields or greater) employing inexpensive, readily available reagents, (i.e., trimethylsilyl chloride and triethylamine). Although H. Vanderhaeghe et al., *Journal of the Chemical Society, Perkin Transactions I*, 932, 1973, describes the epimerization of 6β-phenylacetamidopenicillin-1β-sulfoxide to the corresponding 6α isomer in 87% yield, the process is carried out with N,O-bis(trimethylsilyl)-acetamide (BSA) and 1,5-diazabicyclo [4.3.0]-non-5-ene (DBN) as the reagents, and these reagents are more expensive than the triethylamine and chlorotrimethylsilane used in the present process. Alternatively, Vanderhaeghe et al., *Journal of the Chemical Society, Perkin Transactions I*, 937, 1973 describes the epimerization of benzyl 6β-phenoxyacetamidopenicillanate to the corresponding 6α isomer using trimethylamine and BSA, but only a 38% yield was obtained. The present process overcomes the dual problems of expensive reagents and/or low yields as exemplified by the above two references.

SUMMARY OF THE INVENTION

This invention is directed to an inexpensive and efficient method of epimerizing 6β-acylaminopenicillin-1β-sulfoxides to the corresponding 6α-acylaminopenicillin-1β-sulfoxide stereoisomers. This method entails reacting between about 0.1 to about 4.0 moles of chlorotrimethylsilane and between about 0.1 to about 4 moles of triethylamine per mole of 6β-acylaminopenicillin-1β-sulfoxide in a substantially anhydrous ether or halogenated hydrocarbon solvent, in which solvent the 6β-acylaminopenicillin-1β-sulfoxide is present in a concentration of about 0.7 molar or greater. The process is carried out in a substantially anhydrous atmosphere at a temperature between about −20° C. and about 20° C.

The 6α-acylaminopenicillin-1β-sulfoxides produced by this process are useful intermediates in the synthesis of 7β-acylamino-7α-alkoxy-3-methyl 1-oxa β-lactam acids, a class of 1-oxa β-lactam antibiotics.

DETAILED DESCRIPTION OF THE INVENTION

According to the process of this invention, 6β-acylaminopenicillin-1β-sulfoxides are epimerized with chlorotrimethylsilane and triethylamine to give the corresponding 6α isomer. The process is illustrated by the following generalized scheme:

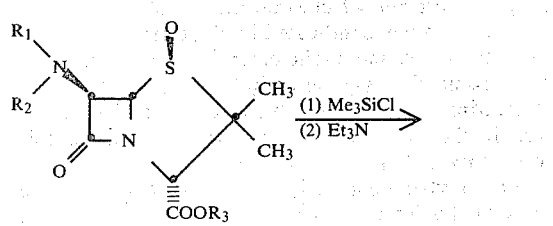

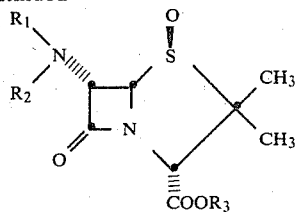

In the above formula, the mark "$\blacksquare$" means β configuration, that is, the group is oriented above the plane of the penicillin ring which is contained in the plane of the paper, and the dotted line "|||" means α-configuration, that is, the group is oriented behind the plane of the penicillin ring.

In the above formula, $R_1$ is hydrogen or an acyl group derived from a carboxylic acid;

$R_2$ is an acyl group derived from a carboxylic acid; or $R_1$ and $R_2$ taken together with the nitrogen atom to which they are attached form a group of the formula

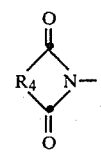

wherein $R_4$ is the residue of an acyl group derived from a dicarboxylic acid;

and $R_3$ is hydrogen or a conventional carboxylic acid protecting group.

Within the above definitions of the C-6 substituents the nature of the carboxylic acid from which these groups are derived is not critical to the present process. The carboxylic acids from which the C-6 substituents are derived are typically $C_1$–$C_{20}$ carboxylic acids. Representative of the C-6 acylamino substituents for the starting materials in the process of the present invention are those conventional in the penicillin and cephalosporin art and includes but are not limited to those described in U.S. Pat. Nos. 3,947,413, 3,932,465; 3,954,732, 3,660,396, 3,948,927, 4,052,387, 4,053,469, 4,058,610, 4,066,641 and 4,042,585. Because of the reactivity of the triethylamine with protic functional groups, for example carboxy, amino and hydroxy groups, such groups, if present on the C-6 side chain moiety of the penicillin substrate, should first be protected using conventional carboxy, amino and hydroxy protecting groups. Alternatively, the unprotected side groups on the C-6 substituent can be protected by the same number of moles of chlorotrimethylsilane as the number of moles of protic substituents present on the C-6 substituent to silylate these protic groups and therefore protect these groups before the triethylamine is added. The amount of chlorotrimethylsilane added to protect the protic groups is in addition to the amount of chlorotrimethylsilane needed to effect the process of the invention.

Conventional amino protecting groups which can be employed in the present invention include the commonly employed amino blocking groups such as the tert-butoxycarbonyl group (t-BOC), the benzyloxycarbonyl group, the 4-methoxybenzyloxycarbonyl group, the 2,2,2-trichloroethoxycarbonyl group, the trimethylsilyl group, and like amino protecting groups. The nature of such amino protecting groups is not critical so long as the protected amino functionality is stable under the reaction conditions described hereinafter.

Conventional hydroxy protecting groups refers any group stable under the reaction conditions of the subsequent step in this synthesis of the 1-oxa β-lactam compounds, but readily cleavable thereafter. Such groups include the formyloxy group, the chloroacetoxy group, the benzhydryloxy group, the trityloxy group, the trimethylsilyl group, and the like.

Protective ester groups denoted as a "conventional carboxylic acid protecting group" or a "carboxy protecting group" that can be employed in this invention include the commonly used carboxylic acid protecting ester groups employed to block or protect the carboxylic acid functionality while reactions involving other functional sites of the compound are carried out. Such protected carboxy groups are noted for their ease of cleavage by hydrolytic or hydrogenolytic methods to the corresponding carboxylic acid. Examples of carboxylic acid protecting groups include tert-butyl, p-methoxybenzyl, diphenylmethyl, 2,4,6-trimethylbenzyl, trityl, 4-methoxytrityl, 4,4'-dimethoxytrityl, 4,4',4''-trimethoxytrityl, trimethylsilyl and like ester forming moieties. The nature of such ester forming groups is not critical so long as the ester formed therewith is stable under the reaction conditions described hereinafter. The p-nitrobenzyl group cannot be used as a carboxy protecting group in the process of this invention.

In the foregoing definitions, hydroxy, amino, and carboxy protecting groups are not exhaustively defined. The function of such groups is to protect the reactive functional groups during the preparation of the desired products and then be removed without disrupting the remainder of the molecule. Many such protecting groups are well known in the art and the use of other groups equally applicable to the process and compounds of the present invention, such as those described in J. F. W. McOmie, "Protective Groups in Organic Chemistry", Plenum Press, 1973, will be recognized as suitable. Thus, there is no novelty or inventiveness asserted with regard to the "protecting groups" alluded to in this specification.

The process of this invention is carried out by reacting at least 0.1 mole of chlorotrimethylsilane and triethylamine each per mole of penicillin substrate in a substantially anhydrous ether or halogenated hydrocarbon in which the 6β-acylaminopenicillin-1β-sulfoxide substrate is present in about 0.7 molar or greater concentration.

The time parameter in the present process is not critical. After addition of the 6β-penicillin-1β-sulfoxide, triethylamine and chlorotrimethylsilane to the ether or halogenated hydrocarbon solvent, the reaction is agitated, for example, with stirring, until the reaction is complete. The course of the epimerization can be followed by thin layer chromatography. For example, a small portion of the reaction mixture can be removed from time to time and a comparative thin layer chromatogram run with starting material and product.

The temperature at which this process can be carried out is between about −20° C. and about 20° C.

Although as described above, at least 0.1 mole of chlorotrimethylsilane per mole of penicillin substrate is required, it is preferable to employ between about 1 to 1.7 moles of chlorotrimethylsilane per mole of the penicillin substrate. These ratios are based on the assumption that all protic groups (ie., amino, hydroxy, carboxy) on the C-6 substituent and the penicillin ring itself have been protected by a conventional protecting group or by adding additional amounts of chlorotrimethylsilane, above what are needed to carry out the process of this invention, in order to protect the protic groups. The chlorotrimethylsilane is used in the present process to silylate the amide function attached to the C-6 position of the penicillin ring, thereby making the C-6 proton more susceptible to removal by the triethylamine base. As mentioned above, the process should be carried out under substantially anhydrous conditions, that is, conditions such that the chlorotrimethylsilane is not hydrolyzed to any significant extent so as to prevent it's participation in the process of this reaction. In that light, all water present in the solvent and the reaction vessel atmosphere needn't be excluded, but only as much as is practical and is needed so as to maintain the high yields afforded by this epimerization process.

As mentioned above, although at least 0.1 mole of triethylamine per mole of the 6β-acylaminopenicillin-1β-sulfoxide substrate is required for the process of this invention, it is preferred that between about 2.2 moles to about 4 moles of triethylamine per mole of penicillin substrate be used. In the event that the C-3 carboxylic acid form of the penicillin is used as the substrate, and the carboxylic acid has not been protected prior to the addition of the triethylamine, (eg., by esterification with chlorotrimethylsilane), it will be necessary to increase the number of moles of triethylamine specified above by the number of moles of the carboxylic acid form of the penicillin substrate present in the solution in order to compensate for the acid-base reaction that will occur between the C-3 carboxylic acid of penicillin substrate and the triethylamine.

Finally, as discussed above, the 6β-acylaminopenicillin-1β-sulfoxide substrate must be at a concentration of about 0.7 molar or above in the process of this invention. This concentration requirement is to assure that the process of this invention occurs within a practical length of time. Of course, the upper limit of the concentration range for the penicillin substrate in the process is when the solution has reached the point of saturation with the penicillin substrate. The preferred concentration range for the 6β-acylaminopenicillin-1β-sulfoxide in this process is between about a 1.25 molar solution to about a 1.85 molar solution.

The epimerization process of this invention is carried out in ether or halogenated hydrocarbon solvents. The ether or halogenated hydrocarbon solvent used in this process should be one in which the 6β-acylaminopenicillin-1β-sulfoxide is at least partially soluble and which does not participate in the reaction, e.g., by reacting with the triethylamine or chlorotrimethylsilane in competition with the penicillin substrate. By "halogenated hydrocarbon" we mean straight, branched or cyclic halogenated alkyl hydrocarbons, and halogenated aromatic hydrocarbons. Examples of such halogenated hydrocarbon solvents include methylene chloride, chloroform, dichloroethane, trichloroethane, 1,1-dibromo-2-chloroethane, chlorobenzene and the like. Solvents indicated by the term "ether" are straight, branched and cyclic ethers such as tetrahydrofuran, dioxane, diethyl ether, dibutyl ether, diglyme and the like. Mixtures of these solvents can likewise be employed in the process. The preferred solvent for this process is methylene chloride.

The 6β-acylaminopenicillin-1β-sulfoxide used in the process of this invention are all known penicillins and can be prepared by methods well known in the art. The first step of one synthesis of the penicillin substrates of the process of this invention would involve acylating 6-aminopenicillanic acid (6-APA) with the appropriate side chain moiety. This reaction could be performed with the side chain in the acid chloride form under Schotten-Bauman conditions or acylation could take place using the side chain in the carboxylic acid form and employing a dehydrating agent such as carbonyldimidazole or dicyclohexylcarbodiimide. A third method would be to convert the side chain substituent to a mixed anhydride and then used to acylate 6-APA.

The resulting 6β-acylaminopenicillanic acid can then be converted to a β-sulfoxide using a wide variety of oxidizing agents, such as ozone, perbenzoic acid, and especially peracetic acid and metachloroperbenzoic acid. Also, inorganic oxidants, such as sodium metaperiodate, can be employed.

An optional step in this example of a synthesis of the penicillin substrate for the process of this invention would be to protect the carboxylic acid at the C-3 position of the 6β-acylaminopenicillanic acid-1β-sulfoxide. As with the previous two steps, this step is well known in the art, and there are many examples of protecting groups which can be used in which different methods can be used to protect the carboxylic acid function. For example, one possible method would be to react a mixed anhydride formed with p-methoxyphenylacetic acid and methyl chloroformate with the 6β-acylaminopenicillanic acid-1β-sulfoxide. Another method would be to react the penicillanic acid sulfoxide substrate with diphenyldiazomethane.

A preferred group of substrates for the process of this invention is when $R_1$ is hydrogen, $R_2$ is an acyl group of the formula

wherein R' is
(a) $C_1$–$C_7$ alkyl, cyanomethyl, $C_1$–$C_6$ haloalkyl, 4-amino-4-carboxybutyl; or
(b) $C_1$–$C_6$ alkoxy, phenoxy, benzyloxy or 4-methoxybenzyloxy; or
(c) the group —R" wherein R" is phenyl or substituted phenyl wherein the substituents are 1 or 2 halogens, hydroxy, cyano, trifluoromethyl, $C_1$–$C_4$ alkyl, $C_1$–$C_4$ alkoxy, carboxy, carboxymethyl, hydroxymethyl or aminomethyl; or
(d) an arylalkyl group of the formula R"—(O)$_m$—CH$_2$— wherein R" is as defined above, and m is 0 or 1; or
(e) a substituted arylalkyl group of the formula

wherein R'" is R" as defined above, 2-thienyl, 3-thienyl, 2-furyl or 3-furyl; W is hydroxy, carboxy, amino, or
(f) a heteroarylmethyl group of the formula R""—CH$_2$— wherein R"" is 2-thienyl, 3-thienyl, 2-furyl, 3-furyl, 2-thiazolyl, 5-tetrazolyl, 1-tetrazolyl;

and $R_3$ is hydrogen, diphenylmethyl, benzyl, p-methoxybenzyl, iodomethyl, tert-butyl, trimethylsilyl, or 2,2,2-trichloroethyl.

In the above description the term "$C_1$–$C_7$ alkyl" refers to methyl, ethyl, n-propyl, n-butyl, isobutyl, pentyl, n-hexyl, cyclohexyl, n-heptyl and like aliphatic hydrocarbon chains.

The term "$C_1$–$C_6$ haloalkyl" refers to chloromethyl, bromomethyl, iodomethyl, 2-bromoethyl, 2-chloroethyl, 2-bromopropyl, 2-iodopropyl, 2-chlorobutyl, 2-bromo-2-methylpropyl, 2-bromobutyl, 2-bromo-2-methylbutyl and like groups.

When in the above definition R" represents a substituted phenyl group, R" can be a mono or disubstituted halophenyl group such as 4-chlorophenyl, 2,6-dichlorophenyl, 2,5-dichlorophenyl, 3,4-dichlorophenyl, 3-chlorophenyl, 3-bromophenyl, 4-bromophenyl, 3,4-dibromophenyl, 3-chloro-4-fluorophenyl, 2-fluorophenyl and the like; a mono or dihydroxyphenyl group such as 4-hydroxyphenyl, 3-hydroxyphenyl, 2,4-dihydroxyphenyl and the like; a cyanophenyl group, for example 4-cyanophenyl; a mono or disubstituted lower alkylphenyl group such as 4-methylphenyl, 2,4-dimethylphenyl, 2-methylphenyl, 4-isopropylphenyl, 4-ethylphenyl, 3-n-propylphenyl and the like; a mono or disubstituted lower alkylphenyl ether for example, 2,6-dimethoxyphenyl, 4-methoxyphenyl, 3-ethoxyphenyl, 4-isopropoxyphenyl, 4-tert-butoxyphenyl, 3-ethoxy-4-methoxyphenyl and the like. Also, R" represents disubstituted phenyl groups wherein the substituents can be different, for example, 3-methyl-4-hydroxyphenyl, 3-chloro-4-hydroxyphenyl, 2-methoxy-4-bromophenyl, 4-ethyl-2-hydroxyphenyl, 3-hydroxy-4-nitrophenyl, 2-hydroxy-4-chlorophenyl and like disubstituted phenyl groups bearing different substituents.

Illustrative of the acyl groups,

wherein R' is $C_1$–$C_7$ alkyl or $C_1$–$C_6$ haloalkyl are acetyl, propionyl, butyryl, hexanoyl, chloroacetyl, bromoacetyl and the like.

Representative of the acyl groups

when R' is phenyl or substituted phenyl are benzoyl, 2,6-dimethoxybenzoyl, 4-chlorobenzoyl, 4-methylbenzoyl, 3,4-dichlorobenzoyl, 4-cyanobenzoyl, 3-bromobenzoyl, 3-aminobenzoyl.

Illustrative of the acyl groups

when R' is a group of the formula R"—(O)$_m$—CH$_2$—, m is 0 and R" is phenyl or substituted phenyl, are phenylacetyl, 4-chlorophenylacetyl, 3-hydroxyphenylacetyl, 3-cyanophenylacetyl, 4-hydroxy-3-methylphenylacetyl, 4-bromophenylacetyl, 4-ethoxyphenylacetyl, 3,4-dimethoxyphenylacetyl and the like; and when m is 1, representative groups are phenoxyacetyl, 3-hydroxyphenoxyacetyl, 4-chlorophenoxyacetyl, 3,4-dichlorophenoxyacetyl, 2-chlorophenoxyacetyl, 4-methoxyphenoxyacetyl, 2-ethoxyphenylacetyl, 3,4-dimethylphenoxyacetyl, 4-isopropylphenoxyacetyl, 3-cyanophenoxyacetyl and like substituted phenoxyacetyl groups.

Illustrative of the acyl groups when R' is a substituted arylalkyl group of the formula

are the carboxy substituted aryl groups such as the 2-carboxy-2-phenylacetyl group of the formula

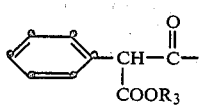

and similar groups wherein the phenyl ring is substituted, for example, 2-carboxy-2-(4-chlorophenyl)acetyl, 2-carboxy-2-(4-methoxyphenyl)acetyl, 2-carboxy-2-(2-thienyl)acetyl, 2-carboxy-2-(4-methylphenyl)acetyl, 2-carboxy-2-(4-(carboxymethyl)phenyl)acetyl, 2-carboxy-2-(4-hydroxymethyl)phenyl)acetyl and like groups.

Representative of the acyl groups when R' is a hydroxy substituted arylalkyl group are 2-hydroxy-2-(4-methoxyphenyl)acetyl, 2-hydroxy-2-(3-chloro-4-hydroxyphenyl)acetyl, 2-hydroxy-2-(3-bromophenyl)acetyl, 2-hydroxy-2-(3,5 dichloro-4-hydroxyphenyl)acetyl, 2-hydroxy-2-(3-chloro-4-methoxyphenyl)acetyl, 2-hydroxy-2-(3-chlorophenyl)acetyl, 2-hydroxy-2-(4-(1-amino-1-methyl)phenyl)acetyl, 2-hydroxy-2-(3-thienyl)-acetyl.

When R' is an amino substituted arylalkyl group, acyl groups represented thereby include 2-amino-2-phenylacetyl, 2-amino-2-(4-cyanophenyl)acetyl, 2-amino-2-(4-hydroxyphenyl)acetyl, and like groups.

Representative of the acyl group

when R' is a heteroarylmethyl group of the formula R''''—CH$_2$— are 2-thienylacetyl, 3-thienylacetyl, 2-furylacetyl, 2-thiazolylacetyl, 1-tetrazolylacetyl, a 5-tetrazolylacetyl and the like.

Examples of the above group of preferred compounds include the following:
 diphenylmethyl 6β-phenylacetamidopenicillanate-1β-sulfoxide,
 diphenylmethyl 6β-phenoxyacetamidopenicillanate-1β-sulfoxide,
 diphenylmethyl 6β-p-methylbenzamidopenicillanate-β-sulfoxide,
 diphenylmethyl 6β-benzamidopenicillanate-1β-sulfoxide,
 6β-phenoxyacetamidopenicillanic acid-1β-sulfoxide,
 p-methoxybenzyl 6β-cyanoacetamidopenicillanate-1β-sulfoxide,
 tert-butyl 6β-(2-phenyl-2-amino)acetamidopenicillanate-1β-sulfoxide,
 benzyl 6β-(1-tetrazolyl)acetamidopenicillanate-1β-sulfoxide,
 2,2,2-trichloroethyl 6β-(2-thiazolyl)acetamidopenicillanate-1β-sulfoxide,
 iodomethyl 6β-(2-thienyl)acetamidopenicillanate-1β-sulfoxide,
 trimethylsilyl 6β-(2-thienyl)acetamidopenicillanate-1β-sulfoxide,
 diphenylmethyl 6β-(2-(p-hydroxyphenyl)-2-amino)acetamidopenicillanate-1β-sulfoxide,
 p-methoxybenzyl 6β-(2-furyl)acetamidopenicillanate-1β-sulfoxide,
 diphenylmethyl 6β-(2-phenyl-2-hydroxy)acetamidopenicillanate-1β-sulfoxide.

A more preferred group of substrates for the process of this invention is defined when R$_1$ is hydrogen, R$_2$ is an acyl group of the formula

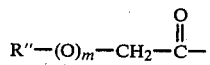

wherein R'' is phenyl or substituted phenyl wherein the substituents are 1 or 2 halogens, hydroxy, cyano, trifluoromethyl, C$_1$-C$_4$ alkyl, C$_1$-C$_4$ alkoxy, carboxy, carboxymethyl, hydroxymethyl or aminomethyl; and n is 0 or 1; and R$_3$ is hydrogen, diphenylmethyl, benzyl, p-methoxybenzyl, iodomethyl, tert-butyl, trimethylsilyl or 2,2,2-trichloroethyl.

Examples of the above more preferred compounds for the process of this invention include:
 diphenylmethyl 6β-phenylacetamidopenicillanate-1β-sulfoxide,
 diphenylmethyl 6β-phenoxyacetamidopenicillanate-1β-sulfoxide,
 diphenylmethyl 6β-benzamidopenicillanate-1β-sulfoxide,
 diphenylmethyl 6β-(p-methoxybenzamido)penicillanate-1β-sulfoxide,
 6β-phenoxyacetamidopenicillanic acid-1β-sulfoxide,
 benzyl 6β-(p-chlorophenylacetamido)penicillanate-1β-sulfoxide,
 p-methoxybenzyl 6β-(o-chlorophenylacetamido)penicillanate-1β-sulfoxide,
 2,2,2-trichloroethyl 6β-(p-trifluoromethylphenylacetamido)penicillanate-1β-sulfoxide,
 tert-butyl 6β-(p-methoxyphenylacetamido)-penicillanate-1β-sulfoxide,
 iodomethyl 6β-(p-carboxyphenylacetamido)-penicillanate-1β-sulfoxide,
 diphenylmethyl 6β-(p-cyanophenylacetamido)-penicillanate-1β-sulfoxide,
 p-methoxybenzyl 6β-(p-aminophenylacetamido)-penicillanate-1β-sulfoxide,
 tert-butyl 6β-(p-hydroxyphenylacetamido)-penicillanate-1β-sulfoxide,
 2,2,2-trichloroethyl 6β-(p-carboxymethylphenylacetamido)penicillanate-1β-sulfoxide,
 diphenylmethyl 6β-(p-aminophenylacetamido)-penicillanate-1β-sulfoxide,
 benzyl 6β-(m-methylphenylacetamido)penicillanate-1β-sulfoxide,
 diphenylmethyl 6β-(o,p-dichlorophenylacetamido)-penicillanate-1β-sulfoxide,
 trimethylsilyl 6β-(o-chloro-p-methoxyphenylacetamido)penicillanate-1β-sulfoxide,
 diphenylmethyl 6β-(p-aminomethylphenylacetamido)penicillanate-1β-sulfoxide,
 p-methoxybenzyl 6β-(p-methylphenoxyacetamido)-penicillanate-1β-sulfoxide, 2,2,2-trichlorethyl 6β-(o-chlorophenoxyacetamido)-penicillanate-1β-sulfoxide, and tert-butyl 6β-(p-aminophenoxyacetamido)-penicillanate-1β-sulfoxide.

A most preferred group of compounds used as the starting materials for the process of this invention is defined where R₁ is hyrogen, R₂ is an acyl group of the formula

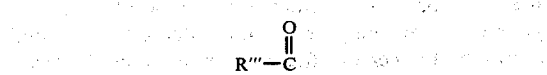

wherein R''' is phenyl, p-methylphenyl, benzyl, or phenoxymethyl and R₃ is hydrogen or diphenylmethyl.

Examples of the above most preferred compounds employed as starting material for the process of this invention are:

diphenylmethyl 6β-phenylacetamidopenicillanate-1β-sulfoxide, diphenylmethyl 6β-phenoxyacetamidopenicillanate-1β-sulfoxide, diphenylmethyl 6β-benzamidopenicillanate-1β-sulfoxide, diphenylmethyl 6β-(p-methylbenzamido)penicillanate-1β-sulfoxide.

and 6β-phenoxyacetamidopenicillanic acid-1β-sulfoxide.

The 6α-acylaminopenicillin-1β-sulfoxides provided by the process are useful intermediates in the synthesis of 1-oxa β-lactam antibiotics, which possess the following bicyclic ring system:

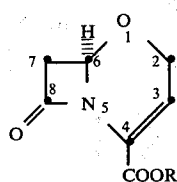

and are described in U.S. Pat. No. 4,138,486.

The first step in the synthesis of the above 1-oxa β-lactam acids from the 6α-acylaminopenicillin-1β-sulfoxide obtained from the process of this invention involves the rearrangement to the corresponding 7α-acylamino-3-methyl-cephalosporin and which is subsequently alkoxylated to give a 7α-acylamino-2α-alkoxy-3-methylcephalosporin.

The alkoxylated cephalosporin is converted to an azetidinone disulfide aldehyde, then reduced to give the corresponding azetidinone disulfide alcohol. The alcohol is cyclized to give a 7α-acylamino-3-methyl 1-oxa β-lactam compound. The newly formed β-lactam compound is subjected to methoxylation to yield the 7β-acylamino-7α-methoxy-3-methyl 1-oxa β-lactam ester, which is deprotected to give the desired carboxylic acid 1-oxa β-lactam antibiotic.

Specifically, the rearrangement of the 6α-acylaminopenicillanate-1β-sulfoxide, obtained from the process of this invention, to the corresponding 7α-acylamino-3-methyl-3-cephem-4-carboxylate, represented by the following general formula,

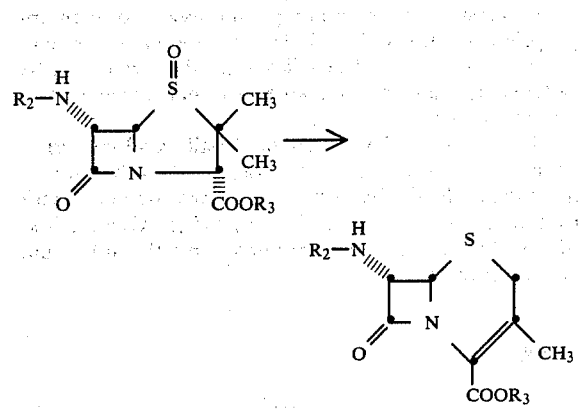

is analogous to a procedure also well known to those skilled in the art. Although several variations of the method are available to effect this rearrangement, the preferred method involves reacting the 6α-acylaminopenicillanate-1-sulfoxide with N,O-bis-(trimethylsilyl)-acetamide(BSA) and α-picoline.HBr in dried dioxane at reflux temperatures. The organic products of the reaction are then extracted into ethyl acetate, the ethyl acetate is evaporated, and the extract is treated with neat pyridine. Pure 7α-acylamino-3-methyl-3-cephem-4-carboxylate can be obtained by recrystallization.

The procedure for the above rearrangement step was adapted from one described by Verweij et al., in U.S. Pat. No. 4,003,894.

The next step in this general reaction scheme involves an α-alkoxylation at the C-2 position of the cephem moiety. This reaction is represented in the following general formula,

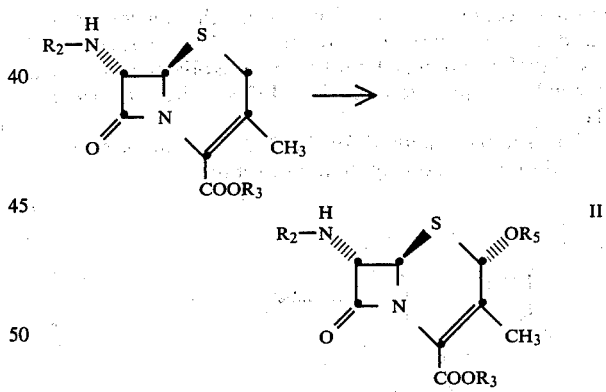

As with the above step in the synthesis of the 1-oxa β-lactam antibiotic, the 2α-alkoxylation reaction involved at this stage of the synthesis is analogous to procedures well known to those skilled in the art; see, for example, D. O. Spry, *Tetrahedron Letters*, 3717 (1972); A. Yoshida, S. Oida, and E. Ohki, *Chemical and Pharmaceutical Bulletin of Japan* (Tokyo), 23, 2507 and 2518 (1975); ibid., 24 362 (1976); ibid., 25, 2082 (1977); C. O. Kim and P. A. McGregor, *Tetrahedron Letters*, 409 (1978). Although the aforementioned references describe various methods of 2α-alkoxylation for 7β-isomers of cephalosporins, the preferred method for the conversion of 7α-acylamino-3-methyl-3-cephem-4-carboxylate to its corresponding 2α-alkoxy analog comprises the addition of N-chlorosuccinimide to a solution of the substrate cephem compound dissolved in an appropriate alcohol and methylene chloride at room temperature. The desired 2α-alkoxy product can then be isolated by standard crystallization and chromatography techniques.

The above 7α-acylamino-2α-alkoxy-3-methyl-3-cephem-4-carboxylate can be converted to the azetidinone disulfide aldehyde by one of two methods, with each method yielding a different product. One method of disulfide formation, represented by the following general formula;

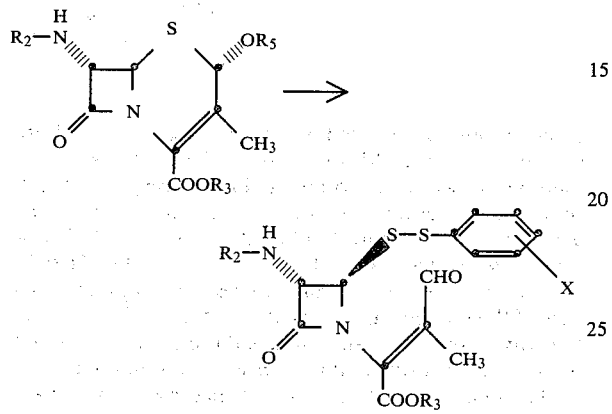

entails adding the 7α-acylamino-2α-alkoxy-3-methyl-3-cephem-4-carboxylate compound to a methylene chloride solution of arylsulfenyl chloride at 0° C. The desired 4β[1-(carboxy protecting group 2-N-3-methyl-4-al-Z-but-2-ene-oate)-2-oxo-3α-acylamino azetidine]disulfide can be reduced at this point to give the unsymmetrical azetidinone disulfide alcohol compound, or may be further purified by conventional chromatographic techniques before submitting the unsymmetrical disulfide aldehydes to reduction. This method for disulfide formation is described by Kukolja and Pfeil in copending application Ser. No. 137,861 filed this even date.

The alternate method for disulfide formation, represented by the following general formula,

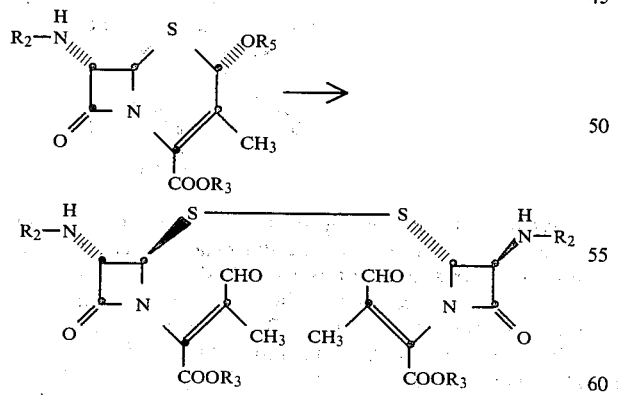

involves adding N-chlorosuccinimide to a methylene chloride solution of the appropriate 7α-acylamino-2α-alkoxy-3-methyl-3-cephem-4-carboxylate compound at 0° C. This solution is then added to an aqueous suspension of mercury dichloride and cadmium carbonate at room temperature. This method of disulfide formation produces a symmetrical disulfide compound that has identically substituted azetidinone moieties bonded to either end of the disulfide group, in contrast with the disulfide formation employing an arylsulfenyl chloride, which produces an unsymmetrical azetidinone disulfide aldehyde compound having an aryl group bonded to one end and an azetidinone moiety bonded to the other end of the disulfide group. The 4β,4'β bis[1-(carboxy protecting group 2-N-3-methyl-4-al-Z-but-2-ene-oate)-2-oxo-3α-acylamino azetidine]disulfide produced in the latter method can be reduced at this point to give the symmetrical azetidinone disulfide alcohol compounds, or may be further purified by conventional chromatographic techniques before submitting these symmetrical azetidinone disulfide aldehydes to reduction.

The next step in the synthesis of the 1-oxa β-lactam compounds involves reducing the symmetrical and unsymmetrical azetidinone disulfide aldehydes with sodium cyanoborohydride to give the corresponding alcohols. This reaction is represented by the following general formulas,

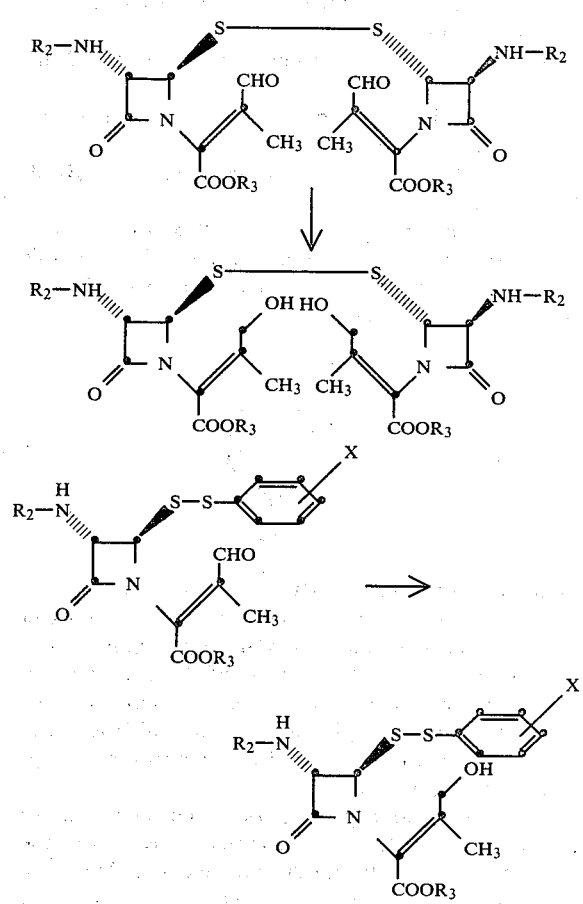

The procedure for this reduction is outlined generally in R. F. Borch, M. D. Bernstein, and H. D. Durst, *Journal of the American Chemical Society*, 93, 2897 (1971) and consists of dissolving the aldehyde compound in aqueous tetrahydrofuran, acidifying the mixture, and then adding the sodium cyanoborohydride reducing agent. The desired alcohol can be purified by conventional extraction techniques.

The symmetrical and unsymmetrical azetidinone disulfide alcohol compounds are subsequently cyclized to give a 1-oxa β-lactam compound, represented by the following general formulas,

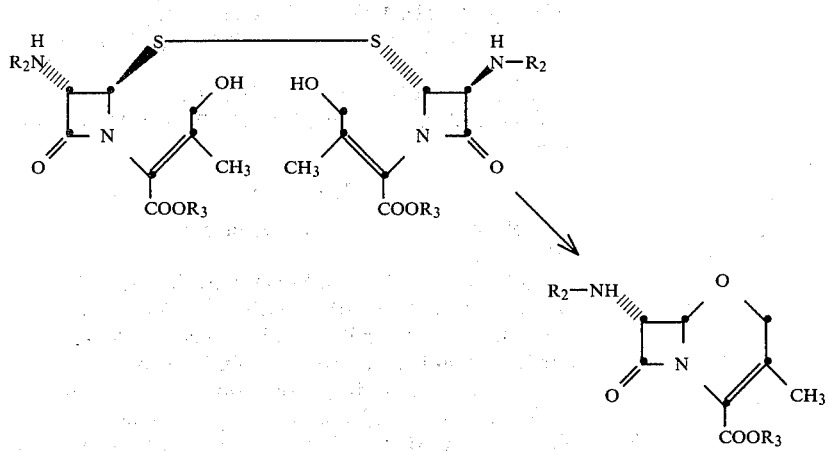

This cyclization is accomplished by reacting the alcohol compounds with a cyclization reagent selected from the group consisting of divalent mercury salts or phosphines. The divalent mercury salts are of the general formula Hg(X)$_2$, where X is chloro, bromo or trifluoroacetato. The mercury cyclization reagent and the substrate alcohol compound are reacted in a dry, polar, inert organic solvent such as acetonitrile. The phosphine cyclization reagent compounds have the general formula

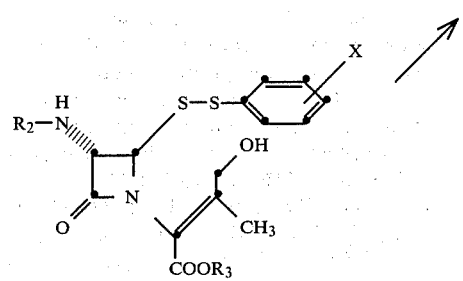

(R$_6$)$_3$P wherein R$_6$ can be alkyl, for example, methyl or ethyl, phenyl or substituted phenyl, for example, 4-methylphenyl. The phosphorus reagent and the substrate alcohol are reacted in a dry, inert, organic solvent such as 1,2-dichloroethane. The desired cyclized product obtained by the use of either class of cyclizing reagent can be purified by conventional chromatographic techniques.

The cyclization of the azetidinone disulfide alcohol compounds to the corresponding 7α-acylamino-3-methyl 1-oxa β-lactam antibiotic is described by Kukolja and Pfeil in copending application Ser. No. 137,862 filed this even date, now U.S. Pat. No. 4,293,493.

The 7α-acylamino-3-methyl 1-oxa β-lactam compound is then converted to the 7β-acylamino-7α-methoxy-3-methyl 1-oxa β-lactam by reacting the 7α-acylamino substrate with lithium methoxide and tert-butyl hypochlorite. This reaction is represented generally by the following formula,

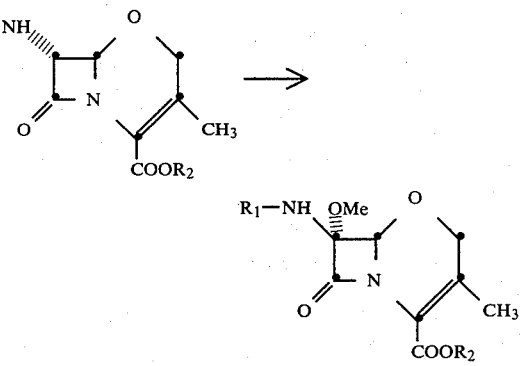

The reaction entails the addition of the 7α-acylamino 1-oxa β-lactam to a suspension of lithium methoxide in dry tetrahydrofuran in an inert atmosphere followed by addition of tert-butyl hypochlorite to the solution to initiate the methoxylation. Once the reaction has reached completion, the reaction is quenched with trimethylphosphite and glacial acetic acid. The desired product can be isolated and purified with conventional liquid-liquid extraction techniques.

The conversion of the 7α-acylamino-3-methyl 1-oxa β-lactam to the 7β-acylamino-7α-methoxy-3-methyl 1-oxa β-lactam ester is carried out in a matter analogous to that of G. A. Koppel and R. E. Koehler, *Journal of the American Chemical Society*, 95, 2403 (1973).

The final step in the synthesis of a 1-oxa β-lactam antibiotic compounds from the 6α-acylaminopenicillin-1β-sulfoxides produced by the process of this invention is to remove the carboxylic acid protecting group from the 7β-acylamino-7α-methoxy-3-methyl 1-oxa β-lactam ester, as shown by the following general formula,

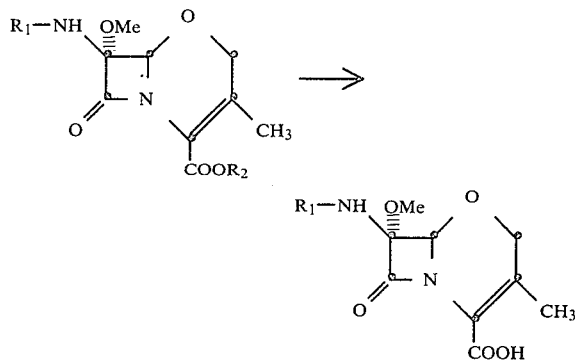

The deprotection step is well known in the art. For example, a method for the deprotection step is described in U.S. Pat. No. 4,138,486.

The following Examples are provided to further illustrate this invention. It is not intended that this invention be limited in scope by reason of any of the examples. In the following examples infrared absorption spectra, nuclear magnetic resonance spectra, ultraviolet absorption spectra and optical rotation spectra are abbreviated i.r., n.m.r., u.v. and o.r., respectively. The nuclear magnetic resonance spectra were obtained on a Varian Associates T-60 Spectrometer using tetramethylsilane as the reference standard. The chemical shifts are expressed in δ values in parts per million (ppm) and coupling constants (J) are expressed as Hz.

All reactions in the following examples were carried out under an atmosphere of nitrogen or argon. In examples one through five, triethylamine and chlorotrimethylsilane were distilled from calcium hydride immediately before use, the methylene chloride used was stored over 4 Å molecular sieves for several days prior to use, and the penicillin sulfoxide substrates were crystallized from the appropriate solvents and dried in vacuo.

EXAMPLE 1

Diphenylmethyl 6α-phenoxyacetamidopenicillanate-1β-sulfoxide.

Diphenylmethyl 6β-phenoxyacetamidopenicillanate-1β-sulfoxide (50.0 g, 94 mmol) was added to methylene chloride (75 ml). Triethylamine (27 ml, 206 mmol) was added and the resultant reaction solution was cooled to 5° C. Chlorotrimethylsilane (13.2 ml, 103 mmol) was added dropwise to the cooled reaction solution and the reaction solution was then stirred for an additional one hour at 5° C. before the solution was allowed to warm to 20° C. over the period of one hour. The heterogeneous reaction mixture was then cooled to 5° C. followed by the dropwise addition of glacial acetic acid (12 ml, 210 mmol). The reaction mixture was diluted with ethyl acetate and extracted 3 times with a hydrochloric acid solution then twice with a saturated sodium bicarbonate solution. The aqueous solutions separated from each of the extractions were extracted with ethyl acetate, and these ethyl acetate extracts were combined with the organic layers separated in the original aqueous extractions and the combined organic extracts were washed with a sodium chloride solution, dried over magnesium sulfate, filtered and evaporated to dryness. The resultant foam was crystallized from a methylene chloride/isopropylether solution then dried in vacuo at 60° C. to give diphenylmethyl 6α-phenoxyacetamidopenicillinate-1β-sulfoxide. (42 g, 84% yield): i.r. (KBr) 3300, 1792, 1755, 1602, 1526, 1499, 1452, 1212, 750, 692 cm$^{-1}$; n.m.r. (CDCl$_3$) δ 1.00 (s, 3H), 1.22 (s, 3H), 4.56 (s, 2H), 4.63 (s, 1H), 4.63 (s, 1H), 5.10 (d, 1H, J=0.8), 5.43 (dd, 1H, J=7, J'=0.8) 6.94 (s, 1H), 7.58 (d, 1H, J=7);

analysis calculated for C$_{29}$H$_{28}$N$_2$O$_6$S: C, 67.42; H, 5.46; N, 5.42; S, 6.21; found: C, 67.67; H, 5.29; N, 5.13; S, 6.01.

EXAMPLE 2

Diphenylmethyl 6α-phenylacetamidopenicillanate-1β-sulfoxide.

Diphenylmethyl 6β-phenylacetamidopenicillanate-1β-sulfoxide (50.0 g, 100 mmol) was added to methylene chloride (80 ml). Triethylamine (30.6 ml, 220 mmol) was added, the reaction solution cooled to −10° C. followed by the dropwise addition of chlorotrimethylsilane (18 ml, 167 mmol). This reaction mixture was allowed to stand at −15° C. for sixteen hours and then poured into hydrochloric acid solution at 0° C. After dilution of the mixture with ethyl acetate (200 ml), crystallization of the product occured. The crystalline product, diphenyl 6α-phenylacetamidopenicillanate-1β-sulfoxide, was isolated by filtration, washed once with water and twice with ether then dried in vacuo. (yield: 39.8 g, 80%): i.r. (KBr) 3300, 1796, 1785, 1756, 1669, 1530, 1498, 1303, 1212, 1172, 695 cm$^{-1}$; n.m.r. (CDCl$_3$) δ 0.86 (s, 3H), 1.48 (s, 3H), 3.53 (s, 2H), 4.50 (s, 1H), 4.95 (d, 1H, J=0.8), 5.11 (dd, 1H, J=7, J'=0.8), 6.59 (d, 1H, J=7), 6.90 (s, 1H):

analysis calculated for C$_{29}$H$_{28}$N$_2$O$_5$S: C, 67.42; H, 5.46; N, 5.42; S, 6.21; found: C, 67.25; H, 5.28; N, 5.20; S, 5.84.

EXAMPLE 3

Diphenylmethyl 6α-benzamidopenicillanate-1β-sulfoxide.

Diphenylmethyl 6β-benzamidopenicillanate-1β-sulfoxide (14.6 g, 30 mmol) was dissolved in methylene chloride (20 ml). Triethylamine (10 ml, 72 mmol) was added and the reaction solution was cooled to 5° C. Chlorotrimethylsilane (4.2 ml, 33 mmol) was added dropwise to the reaction solution, and the resultant reaction mixture was stirred at 5° C. for one hour, at the end of which time the temperature of the reaction mixture was allowed to reach 20° C. over a four hour period. The reaction mixture was diluted with ethyl acetate (150 ml) and then extracted twice with hydrochloric acid solution and once with saturated brine solution. The organic layer in the above extracts was separated, dried over magnesium sulfate, filtered, and evaporated to dryness. The resultant foam was crystallized from methylene chloride/isopropyl ether and the crystals dried in vacuo to give pure diphenylmethyl 6α-benzamidopenicillanate-1β-sulfoxide (12.8 g, 88% yield): i.r. (KBr) 3320, 1789, 1752, 1657, 1533, 1492, 1271, 1220, 1178, 1030, 758, 500 cm$^{-1}$; n.m.r. (CDCl$_3$) δ 0.94 (s, 3H), 1.15 (s, 3H), 4.63 (s, 1H) 5.18 (d, 1H, J=0.8), 5.45 (dd, 1H, J=7, J'=0.8) 6.94 (s, 1H);

analysis calculated for C$_{28}$H$_{26}$N$_2$O$_5$S: C, 66.92; H, 5.21; N, 5.57; s, 6.38; found: C, 66.66; H, 5.15; N, 5.32; S, 6.37.

EXAMPLE 4

6α-Phenoxyacetamidopenicillanic acid-1β-sulfoxide.

6β-Phenoxyacetamidopenicillanic acid-1β-sulfoxide (10 g, 27.3 mmol) was added to methylene chloride (15 ml). To the resultant slurry was added chlorotrimethylsilane (3.5 ml, 27.3 mmol) then the reaction mixture was cooled to −20° C. Triethylamine (15.2 ml, 109.2 mmol) was added dropwise, followed 5 minutes later by addition of more chlorotrimethylsilane (3.5 ml, 27.3 mmol). The cooling bath was removed and the reaction mixture was stirred for 3.5 hours at ambient temperature. Glacial acetic acid (3.1 ml, 54.6 mmol) was added to the reaction mixture, which was then diluted with ethyl acetate (75 ml). The resulting solution was washed once with a saturated sodium bicarbonate solution (8.024 g, 3.5 equivalents) then once with water. The separated aqueous layers from the above washings were washed with methylene chloride then acidified to pH 2.2 with six molar hydrochloric acid solution. The acidified aqueous extracts were placed in the refrigerator overnight. The above methylene chloride wash was evaporated to dryness, then the residue redissolved in ethyl acetate and the ethyl acetate solution was extracted with a sodium bicarbonate solution. The separated sodium bicarbonate layer's pH was adjusted to 2.2 with 6 molar hydrochloric acid solution and placed in the refrigerator overnight. The resulting crystalline acidic material was collected by filtration, combined and dried in vacuo to yield 6α-phenoxyacetamidopenicillanic acid-1β-sulfoxide monohydrate (9.2 g, 97% yield): i.r. (KBr) 3560, 3518, 3240, 1770, 1722, 1683, 1555, 1498, 1302, 1245, 1085, 1069, 997, 755 cm$^{-1}$; n.m.r. (DMSO-d$_6$) δ 1.19 (s, 3H), 1.51 (s, 3H), 4.21 (s, 1H), 4.53 (s, 2H), 5.15 (dd, 1H, J=7, J'=0.8), 9.23 (d, 1H, J=7);

analysis calculated for $C_{16}H_{20}N_2O_7S$: C, 49.99; H, 5.24; N, 7.29; S, 8.34; found: C, 50.06, H, 5.46; N, 7.15; S, 8.22.

EXAMPLE 5

Diphenylmethyl 6α-(p-toluylamido)penicillanate-1β-sulfoxide.

Diphenylmethyl 6β-(p-toluylamido)penicillanate-1β-sulfoxide (25.8 g, 50 mmol) was added to methylene chloride (31 ml). After cooling this solution to −15° C., triethylamine (16.8 ml, 120 mmol) was added dropwise over a ten minute period. Chlorotrimethylsilane (8.9 ml, 70 mmol) was added dropwise over an eleven minute period and the resultant reaction mixture was stirred at −10° C. for six hours. The reaction solution was then extracted by adding it to one molar hydrochloric acid (170 ml) followed by addition of methylene chloride (93 ml). The resultant partition was shaken and the layers were separated. The aqueous layer was extracted with additional methylene chloride (15 ml) resultant organic layer was combined with the organic layer from the previous extraction. The pH of the aqueous phase was adjusted to the 6.5 to 7.0 range by the addition of water (100 ml) and dilute sodium hydroxide solution. The aqueous phase was again extracted with methylene chloride, and the resultant organic layer was combined with the previous organic extracts. Toluene (100 ml) was added to the combined methylene chloride extracts, and the methylene chloride was removed under a vacuum. The remaining toluene solution was placed in the refrigerator for 30 min., giving crystals of the desired product which were isolated by filtration and dried under vacuum to give diphenylmethyl 6α-toluylamido)-penicillanate-1β-sulfoxide (21.3 g, 82.5% yield): m.p. 159°-161° C.; i.r. (KBr) 3320, 1781, 1748, 1651, 1608, 1532, 1500, 1273, 1223, 1182, 760, 705 cm$^{-1}$, n.m.r. (CDCl$_3$) δ 0.92 (s, 3H), 1.63 (s, 3H), 2.36 (s, 3H) 4.63 (s, 1H), 5.5 (d, 1H, J=0.8), 5.42 (dd, 1H, J=7, J'=0.8), 6.97 (s, 1H), 7.73 (d, 1H, J=7);

analysis calculated for $C_{29}H_{28}N_2O_5S$: C, 67.42; H, 5.46; N, 5.42; S, 6.21; found: C, 67.71; H, 5.72; N, 5.69; S, 5.89.

EXAMPLE 6

Diphenylmethyl 6α-(p-toluylamido)penicillanate-1β-sulfoxide.

Diphenylmethyl 6β-(p-toluylamido)penicillanate-1β-sulfoxide (258 g, 0.5 moles) was dissolved in methylene chloride (300 ml). The resultant solution was cooled to −15° C. and triethylamine (210 ml, 1.5 moles) was added dropwise over a fifty-five minute period to the stirring solution. Chlorotrimethylsilane (95 ml, 0.75 moles) was then added dropwise to the stirred solution over a twenty-five minute period. The resultant reaction solution was then stirred at −10° C. for 5 hrs. Methylene chloride (500 ml) was added to the reaction flask, the resultant solution was cooled to −10° C., and one molar hydrochloric acid (500 ml) at 0° C. was added to this solution followed by stirring. An additional portion of one molar HCl (400 ml) at 0° C. was added and the resultant partition was shaken, the layers separated and the aqueous acidic layer was discarded. The methylene chloride layer was extracted with an additional one molar hydrochloric acid (100 ml) at 0° C., the layers were separated, and the aqueous acid layer was again discarded. Water (700 ml) was added to the methylene chloride layer and the combination was stirred vigorously. The pH of the solution was adjusted to 6.8 by the addition of dilute sodium hydroxide solution, and the layers were separated. The methylene chloride layer was dried with magnesium sulfate then filtered. The methylene chloride was removed in steps by evaporation of part of the methylene chloride under vacuum, addition of methanol (500 ml), and repetition of these steps twice to remove all of the methylene chloride. The methanol solution was placed in the refrigerator for two days, the crystals of the desired product were isolated by filtration, washed with methanol and dried at 40° C. under vacuum to give diphenyl 6α-(p-toluylamido)penicillanate-1β-sulfoxide (221 g, 0.43 moles, 86% yield). The spectral properties for the compound obtained in this example are the same as those for the compound obtained in Example 5.

I claim:

1. A process for preparing a compound of the formula I

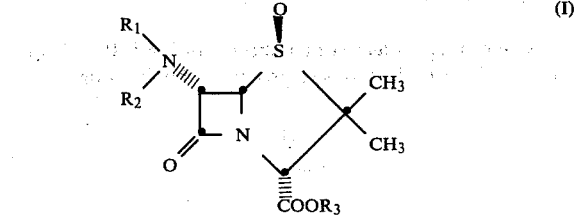

which comprises reacting between about 0.1 to about 4 moles of triethylamine and between about 0.1 to about 4 moles of chlorotrimethylsilane per mole of 6β-acylaminopenicillin-1β-sulfoxide compound of the following formula (II)

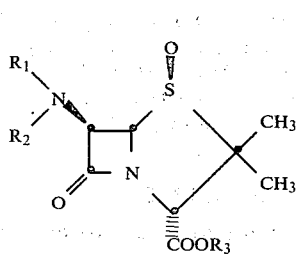

in a substantially anhydrous ether or halogenated hydrocarbon solvent, in which solvent the above 6β-acylaminopenicillin-1β-sulfoxide (II) is present in a concentration of about 0.7 molar or greater, in a substantially anhydrous atmosphere at a temperature between about −20° C. and about 20° C. where in the above formulas R₁ is hydrogen or an acyl group derived from a carboxylic acid; and R₂ is an acyl group derived from a carboxylic acid; or R₁ and R₂ taken together with the nitrogen atom to which they are attached form a group of the formula

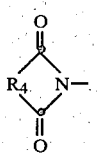

wherein R₄ is the residue of an acyl group derived from a dicarboxylic acid; and R₃ is hydrogen or a conventional carboxylic acid protecting group;

2. The process of claim 1 wherein R₁ is hydrogen, and R₂ is an acyl group of the formula

wherein R' is
(a) C₁–C₇ alkyl, cyanomethyl, C₁–C₆ haloalkyl or, 4-amino-4-carboxybutyl; or
(b) C₁–C₆ alkoxy, phenoxy, benzyloxy or 4-methoxybenzyloxy; or
(c) the group —R" wherein R" is phenyl or substituted phenyl wherein the substituents are 1 or 2 halogens, hydroxy, cyano, trifluoromethyl, C₁–C₄ alkyl, C₁–C₄ alkoxy, carboxy, carboxymethyl, hydroxymethyl or aminomethyl; or
(d) an arylalkyl group of the formula

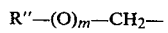

wherein R" is as defined above, and m is 0 or 1; or
(e) a substituted arylalkyl group of the formula

wherein R'" is R" as defined above, 2-thienyl, 3-thienyl, 2-furyl or 3-furyl; W is hydroxy, carboxy, amino; or
(f) a heteroarylmethyl group of the formula

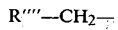

wherein R"" is 2-thienyl, 3-thienyl, 2-furyl, 3-furyl, 2-thiazolyl, 5-tetrazolyl, or 1-tetrazolyl; and R₃ is a carboxy protecting group or hydrogen.

3. The process of claim 2 wherein R₂ is an acyl group of the formula

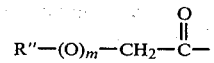

wherein R" is phenyl or substituted phenyl wherein the substituents are 1 or 2 halogens, hydroxy, cyano, trifluoromethyl, C₁–C₄ alkyl, C₁–C₄ alkoxy, carboxy, carboxymethyl, hydroxymethyl or aminomethyl; and m is 0 or 1.

4. The process of claim 3 wherein the initial concentration of 6β-acylaminopencillin-1β-sulfoxide is between about a 1.25 molar solution and about a 1.85 molar solution.

5. The process of claim 4 in which the ratio of moles of chlorotrimethylsilane to the moles of amido, amine, hydroxy or carboxy acid functions present in the 6β-acylaminopencillin-1β-sulfoxide is between about 1 to 1 and about 1.7 to 1.

6. The process of claim 5 wherein the ratio of moles of triethylamine to moles of the 6β-acylaminopenicillin-1β-sulfoxide is between about 2.2 to 1 and about 4 to 1.

7. The process of claim 6 wherein R₂ is an acyl group of the formula

and R' is phenyl, p-methylphenyl, benzyl or phenoxymethyl.

8. The process of claim 1 wherein the ratio of moles of chlorotrimethylsilane to the moles of amido, amine, hydroxy or carboxy acid functions present in the 6β-acylaminopenicillin-1β-sulfoxide is between about 1 to 1 and about 1.7 to 1, and where the ratio of moles of triethylamine to moles of the 6β-acylaminopenicillin-1β-sulfoxide is between about 2.2 to 1 and about 4 to 1.

9. The process of claim 1 wherein the initial concentration of the 6β-acylaminopenicillin-1β-sulfoxide is between about a 1.25 molar solution and about a 1.85 molar solution.

10. The process of claim 9 wherein the ratio of moles of chlorotrimethylsilane to the moles of amido, amine, hydroxy or carboxy acid functions present in the 6β-acylaminopenicillin-1β-sulfoxide is between about 1 to 1 and about 1.7 to 1.

11. The process of claim 10 wherein the ratio of moles of triethylamine to moles of the 6β-acylaminopenicillin-1β-sulfoxide is between about 2.2 to 1 and about 4 to 1.

12. The process of claim 11 wherein R₁ is hydrogen; and R₂ is an acyl group of the formula

wherein R' is
(a) C₁–C₇ alkyl, cyanomethyl, C₁–C₆ haloalkyl, or 4-amino-4-carboxybutyl; or
(b) C₁–C₆ alkoxy, phenoxy, benzyloxy or 4-methoxybenzyloxy; or (c) the group —R″ wherein R″ is phenyl or substituted phenyl, wherein the substituents are 1 or 2 halogens, hydroxy, cyano, trifluoromethyl, $C_1$–$C_4$ alkyl, $C_1$–$C_4$ alkoxy, carboxy, carboxymethyl, hydroxymethyl or aminomethyl; or (d) an arylalkyl group of the formula $$R''{-}(O)_m{-}CH_2{-}$$

wherein R″ is as defined above, and m is 0 or 1; or (e) a substituted arylalkyl group of the formula $$R'''{-}\underset{W}{\overset{H}{\underset{|}{\overset{|}{C}}}}{-}$$

wherein R‴ is R″ as defined above, 2-thienyl, 3-thienyl, 2-furyl or 3-furyl; W is hydroxy, carboxy, amino; or (f) a heteroarylmethyl group of the formula $$R''''{-}CH_2{-}$$

wherein R″″ is 2-thienyl, 3-thienyl, 2-furyl, 3-furyl, 2-thiazolyl, 5-tetrazolyl, or 1-tetrazolyl;

and $R_3$ is a carboxy protecting group or hydrogen.

13. The process of claim 12 wherein $R_2$ is an acyl group of the formula $$R''{-}(O)_m{-}CH_2{-}\overset{O}{\overset{\|}{C}}{-}$$

wherein R″ is phenyl or substituted phenyl wherein the substituents are 1 or 2 halogens, hydroxy, cyano, trifluoromethyl, $C_1$–$C_4$ alkyl, $C_1$–$C_4$ alkoxy, carboxy, carboxymethyl, hydroxymethyl or aminomethyl; and m is 0 or 1.

14. The process of claim 13 where $R_2$ is an acyl group of the formula $$R'{-}\overset{O}{\overset{\|}{C}}{-}$$

and R′ is phenyl, p-methylphenyl, benzyl and phenoxymethyl.

15. The process of claim 7 or 14 in which $R_2$ is an acyl group of the formula $$B{-}\overset{O}{\overset{\|}{C}}{-}$$

and B is p-methylphenyl.

16. The process of claim 15 wherein the solvent used is methylene chloride.

17. The process of claim 16 wherein the temperature of the reaction solution is between about −15° C. and about −10° C.

18. The process of claim 17 wherein the ratio of moles of chlorotrimethylsilane to the moles of the 6β-p-methylphenylcarbonylaminopenicillin-1β-sulfoxide is about 1.5 to 1.

19. The process of claim 18 wherein the ratio of moles of triethylamine to the moles of the 6β-p-methylphenylcarbonylaminopenicillin-1β-sulfoxide is about 3 to 1.

20. The process of claim 19 wherein $R_3$ is diphenylmethyl.

21. The process of claim 20 wherein the initial concentration of the 6β-p-methylphenylcarbonylaminopenicillin-1β-sulfoxide is about a 1.67 molar solution.

22. The process of claim 16 wherein the temperature of the reaction solution is about −10° C.

23. The process of claim 22 wherein the ratio of moles of chlorotrimethylsilane to the moles of the 6β-p-methylphenylcarbonylaminopenicillin-1β-sulfoxide is about 1.4 to 1.

24. The process of claim 23 wherein the ratio of moles of triethylamine to the moles of the 6β-p-methylphenylcarbonylaminopenicillin-1β-sulfoxide is about 2.4 to 1.

25. The process of claim 24 wherein $R_3$ is diphenylmethyl.

26. The process of claim 25 wherein the initial concentration of the 6β-p-methylphenylcarbonylaminopenicillin-1β-sulfoxide is about a 1.61 molar solution.

27. The process of claims 7 or 14 wherein $R_2$ is an acyl group of the formula $$D{-}\overset{O}{\overset{\|}{C}}{-}$$

and D is phenyl.

28. The process of claim 27 wherein the solvent used is methylene chloride.

29. The process of claim 28 wherein the temperature of the reaction solution is about 5° C.

30. The process of claim 29 where the ratio of moles of chlorotrimethylsilane to the moles of 6β-phenylcarbonylaminopenicillin-1β-sulfoxide is about 1.1 to 1.

31. The process of claim 30 wherein the ratio of moles of triethylamine to the moles of 6β-phenylcarbonylaminopenicillin-1β-sulfoxide is about 2.4 to 1.

32. The process of claim 31 wherein $R_3$ is diphenylmethyl.

33. The process of claim 32 wherein the initial concentration of the 6β-phenylcarbonylaminopenicillin-1β-sulfoxide is about a 1.5 molar solution.

34. The process of claims 7 or 14 wherein $R_2$ is an acyl group of the formula $$E{-}\overset{O}{\overset{\|}{C}}{-}$$

and E is benzyl.

35. The process of claim 34 wherein the solvent used is methylene chloride.

36. The process of claim 35 wherein the temperature of the reaction solution is about −15° C.

37. The process of claim 36 wherein the ratio of moles of chlorotrimethylsilane to the moles of the 6β-benzylcarbonylaminopenicillin-1β-sulfoxide is about 1.67 to 1.

38. The process of claim 37 wherein the ratio of moles of triethylamine to the moles of the 6β-benzylcarbonylaminopenicillin-1β-sulfoxide is about 2.2 to 1.

39. The process of claim 38 wherein $R_3$ is diphenylmethyl.

40. The process of claim 39 wherein the initial concentration of the 6β-benzylcarbonylaminopenicillin-1β-sulfoxide is about a 1.25 molar solution.

41. The process of claims 7 or 14 wherein $R_2$ is an acyl group of the formula

wherein G is of the formula

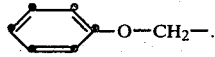

42. The process of claim 41 wherein the solvent used is methylene chloride.

43. The process of claim 42 wherein the temperature of the reaction solution is about 5° C. to about 20° C.

44. The process of claim 43 wherein the ratio of moles of chlorotrimethylsilane to the moles of the 6β-phenoxymethylcarbonylaminopenicillin-1β-sulfoxide is about 1.1 to 1.

45. The process of claim 44 wherein the ratio of moles of triethylamine to the moles of the 6β-phenoxymethylcarbonylaminopenicillin-1β-sulfoxide is about 2.2 to 1.

46. The process of claim 45 wherein $R_3$ is diphenylmethyl.

47. The process of claim 46 wherein the initial concentration of the 6β-phenoxymethylcarbonylaminopenicillin-1β-sulfoxide is about a 1.25 molar solution.

48. The process of claim 42 wherein the temperature of the reaction solution is between about −20° C. to about 20° C.

49. The process of claim 48 wherein the ratio of moles of chlorotrimethylsilane to the moles of the 6β-phenoxymethylcarbonylaminopenicillin-1β-sulfoxide is about 2 to 1.

50. The process of claim 49 wherein the ratio of moles of triethylamine to the moles of 6β-phenoxymethylcarbonylaminopenicillin-1β-sulfoxide is about 4 to 1.

51. The process of claim 50 wherein $R_3$ is hydrogen.

52. The process of claim 51 wherein the initial concentration of the 6β-phenoxymethylcarbonylaminopenicillin-1β-sulfoxide is about a 1.82 molar solution.

* * * * *